(12) United States Patent
Khibnik et al.

(10) Patent No.: US 8,459,103 B2
(45) Date of Patent: Jun. 11, 2013

(54) IDMS SIGNAL PROCESSING TO DISTINGUISH INLET PARTICULATES

(75) Inventors: Alexander I. Khibnik, Glastonbury, CT (US); Ravi Rajamani, West Hartford, CT (US); Coy Bruce Wood, Ellington, CT (US); Rajendra K. Agrawal, South Windsor, CT (US); William Donat, Manchester, CT (US)

(73) Assignee: United Technologies Corporation, Hartford, CT (US)

( * ) Notice: Subject to any disclaimer, the term of this patent is extended or adjusted under 35 U.S.C. 154(b) by 84 days.

(21) Appl. No.: 13/168,293

(22) Filed: Jun. 24, 2011

(65) Prior Publication Data

US 2012/0324987 A1    Dec. 27, 2012

(51) Int. Cl.
*G01M 15/14*    (2006.01)
(52) U.S. Cl.
USPC .................................................. 73/112.01
(58) Field of Classification Search
USPC .................................................. 73/112.01
See application file for complete search history.

(56) References Cited

U.S. PATENT DOCUMENTS

| 4,888,948 | A | 12/1989 | Fisher et al. |
| 5,070,722 | A | 12/1991 | Hawman et al. |
| 5,164,236 | A | 11/1992 | Schmid |
| 6,668,655 | B2 * | 12/2003 | Harrold et al. ................. 73/660 |
| 7,275,415 | B2 | 10/2007 | Rhodes et al. |
| 7,895,818 | B2 | 3/2011 | Snell et al. |
| 8,074,498 | B2 * | 12/2011 | Agrawal et al. ............ 73/112.01 |
| 8,256,277 | B2 * | 9/2012 | Khibnik et al. ............ 73/112.01 |
| 2008/0016971 | A1 | 1/2008 | Bunce et al. |
| 2009/0112519 | A1 * | 4/2009 | Novis et al. ................... 702/183 |
| 2010/0287907 | A1 * | 11/2010 | Agrawal et al. ............ 60/39.091 |
| 2011/0079015 | A1 * | 4/2011 | Geis et al. ....................... 60/779 |
| 2011/0179763 | A1 * | 7/2011 | Rajamani et al. .......... 60/39.092 |

FOREIGN PATENT DOCUMENTS

| EP | 1978222 A2 | 10/2008 |
| WO | WO9839671 | 9/1998 |

* cited by examiner

*Primary Examiner* — Freddie Kirkland, III
(74) *Attorney, Agent, or Firm* — Kinney & Lange, P.A.

(57) ABSTRACT

A method for operating a debris monitoring system comprises continuously sensing the passage of particulates through a gas turbine engine to produce a time-domain sensor signal. The time-domain sensor signal is Fourier transformed to produce a frequency domain sensor signal. The frequency domain sensor signal is partitioned into bins corresponding to particulate composition categories. At least one feature is identified within each bin, and is used to determine the amount of particulate flow in each particulate composition category.

23 Claims, 3 Drawing Sheets

IDMS SIGNAL PROCESSING TO DISTINGUISH INLET PARTICULATES

BACKGROUND

The present invention relates generally to signal processing, and more specifically to signal processing for inlet debris monitoring systems for gas turbine engines.

Gas turbine engines draw in and compress environmental air. Aircraft gas turbines may operate in a wide range of environments, including environments wherein environmental air contains debris particulates, such as sand or ice, which can be harmful to turbine components.

Gas turbine engines for aircraft commonly include an inlet debris monitoring system (IDMS) which monitors ingestion of charge-carrying debris, and notifies pilots or updates a maintenance log in the event of discrete debris ingestion. Conventional IDMSs include electrostatic sensors which inductively sense the passage of charged particles, and produce sensor signals proportional to the magnitude of charge on ingested debris. These sensors can take several forms, such as buttons or rings of conductive material within or surrounding turbine air passages. Signals from these sensors are conventionally digitized and analyzed in the time domain to determine when debris events occur, how long debris events last, and the approximate overall rate of debris flow. Similar debris monitoring systems have conventionally been used to monitor debris both in turbine inlets and outlets. Conventional signal processing techniques are not capable of characterizing flow of small particulates which cannot be discretely sensed. While discrete debris ingestion produces relatively sharp time-domain signal peaks corresponding to each ingested debris piece, flow of smaller particulates such as sand or dust produces a broad band debris sensor signal. Conventional signal analysis systems and methods cannot reliably characterize the flow rate and composition of ingested particulate material, including for the purposes of damage estimation and prognosis.

SUMMARY

The present invention is directed toward a system and method for debris monitoring. At least one sensor continuously monitors passage of particulates through a gas turbine engine to produce a time-domain sensor signal. The time-domain sensor signal is Fourier transformed to produce a frequency domain sensor signal. The frequency domain sensor signal is partitioned into bins corresponding to particulate composition categories. At least one feature is identified within each bin, and is used to determine the amount of particulate flow of each particulate composition category.

DETAILED DESCRIPTION

Figure 1:
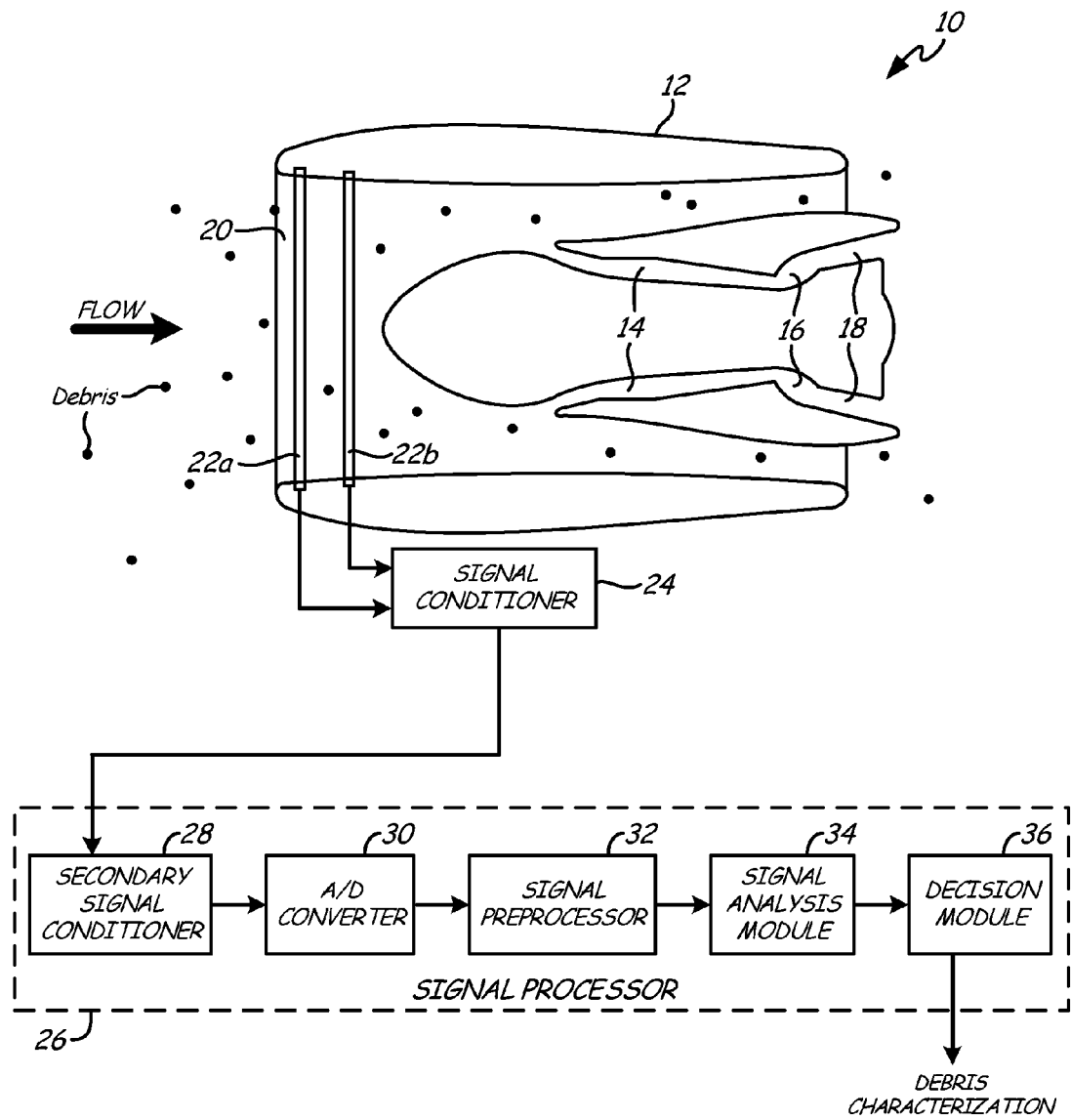
FIG. 1 is a cross-sectional and block diagram of a debris monitoring system of the present invention.

FIG. 1 depicts debris monitoring system 10 for gas turbine engine 12. Gas turbine engine 12 is an aircraft gas turbine engine with compressor 14, combustor 16, turbine 18, and inlet 20. Debris monitoring system 10 comprises debris sensors 22a and 22b, signal conditioner 24, and signal processor 26, which includes secondary signal conditioner 28, analog/digital converter 30, signal analysis module 34, and decision module 36.

Gas turbine engine 12 is a conventional gas turbine engine which takes in air via inlet 20, compresses that air at compressor 14, injects fuel into this compressed air and combusts the resulting fuel/air mixture at combustor 16, and extracts energy from the resulting air pressure at turbine 18. In FIG. 1, air flows from left to right through gas turbine engine 12, as shown. Debris sensors 22a and 22b produce sensor signals in response to debris passing through inlet 20. Signal conditioner 24 receives these sensor signals and conditions them for processing and analog-to-digital conversion. Signal processor 26 receives and interprets conditioned sensor signals, producing an output debris characterization which may be stored in a maintenance log, or monitored in an aircraft cockpit. Signal processor 26 may, for instance, be an aircraft electronic engine controller or a prognostic health monitoring unit. Signal processor 26 may be located on an aircraft carrying gas turbine engine 12, or may be located at a remote location, such as a maintenance facility. If signal processor 26 is located at a remote location, debris monitoring system 10 may include data storage (not shown) for archiving signals for later processing.

Debris, including small particulates, is sometimes carried by airflow into gas turbine 12. This debris may, for instance, comprise sand, dust, or ice. At least one debris sensor monitors the passage of debris at inlet 20. The depicted system includes two such sensors: debris sensor 22a and debris sensor 22b. In the depicted embodiment, debris sensors 22a and 22b are electrostatic ring sensors which monitor fluctuations in electromagnetic field through the plane of the ring. Thus, charged particulates induce a time-domain signal current by passing through debris sensors 22a and 22b. In alternative embodiments debris sensors 22a and 22b may be other types of sensors, such as electrostatic button sensors. Although electrostatic sensors are conventionally used to monitor debris ingestion, the signal processing methodology described herein will be understood by those skilled in the art to be applicable to other sensor signals as well. In embodiments using only electrostatic sensors, debris sensors 22a and 22b cannot detect uncharged debris. Most ingested debris carries at least some electrostatic charge, but any uncharged debris will pass through inlet 20 undetected. In some embodiments debris sensors 22a and 22b are substantially identical. In alternative embodiments, an array of dissimilar sensors may be used.

Signal conditioner 24 receives signal currents produced by debris sensors 22a and 22b, removes predictable background noise, amplifies resulting signals, and transmits resulting conditioned signals to signal processor 26. Signal processor 26 produces a debris characterization from the conditioned signal provided by signal conditioner 24. This debris characterization may be stored in a log for retrieval during maintenance of gas turbine engine 12, or forwarded to an aircraft cockpit, or both. In some embodiments the debris characterization will only be stored or forwarded to the cockpit if a debris event is recognized, such a large flow volume of particulates, or an individual discrete large or potentially damaging debris object ingestion. The debris characterization includes not only a sensed debris ingestion volume, but a profile of particulate mass flow rate as a function of particulate composition and time. Particulate composition reported in the debris characterization can include both particulate size and material. The debris characterization may include a single timestamp associated with an average mass flow rate profile as a function of composition, or may include a plurality of higher resolution time periods.

Debris of different sizes can differently affect each component. For this reason, it is helpful to distinguish between particulate flow rates for different particulate sizes or size ranges. Similarly, particulates of different materials may cause more or less damage, wear, or performance loss of different kinds. Fine particulates, for instance, may pose a greater risk of clogging, while large, hard particulates may cause increased erosion.

Signal processor 26 includes secondary signal conditioner 28, analog/digital converter 30, signal preprocessor 32, signal analysis module 34, and decision module 36.

Secondary signal conditioner 28 performs additional signal conditioning to correct signal distortion or corruption between signal conditioner 24 and signal processor 26. Particularly when signal processor 26 is located remotely from signal conditioner 24, predictable noise or distortion can be introduced between signal conditioner 24 and signal processor 26; secondary signal conditioner 28 corrects for these effects. Analog/digital converter 30 digitizes the output of secondary signal conditioner 28

Signal preprocessor 32 performs additional signal filtering on the digitized sensor signal produced by analog/digital converter 30. In particular, while signal conditioner 24 generally conditions sensor signals for analysis by signal processor 26, as described above, signal preprocessor 32 provides algorithm-specific filtering which conditions sensor signals for particular algorithms used by signal analysis module 34. The filter functions applied by signal preprocessor 32 are matched to the algorithms performed by signal analysis module 34, and can be changed if signal analysis module 34 switches algorithms. Signal preprocessor 32 can, for instance, apply filters to reduce noise, clean the digital signal to eliminate or reduce statistical outliers, discard data corresponding to outlying frequencies or unexpected voltages, and normalize or down-sample resulting signals.

Signal analysis module 34 and decision module 36 may comprise separate hardware components of signal processor 26, or may comprise separate software or logical components which run on shared hardware such as a microprocessor. Signal analysis module 34 Fourier transforms the sensor signal, subdivides the sensor signal into bins corresponding to particulate composition categories, and identifies features of the sensor signal in each bin.

The signal output of preprocessor 32, like the output of debris sensors 22a and 22b, is a time-domain signal with amplitude or energy corresponding to debris ingestion volume. Signal analysis module 34 Fourier transforms this time-domain signal to produce a frequency-domain signal. Signal analysis module 34 then divides this frequency-domain signal into a plurality of bins. These bins may, for instance, be frequency ranges of the frequency-domain sensor signal, as described with respect to FIG. 3. Such bins can cover regular, overlapping or non-overlapping ranges, or can cover dynamically updated frequency ranges specified by signal analysis module 34 in response to characteristics of the digitized sensor signal. Each bin corresponds to a particle composition range, with higher frequencies generally corresponding to smaller particulates, and lower frequencies corresponding to larger particulates.

Within each bin, signal analysis module 34 extracts one or more primary signal features such as signal amplitude (maximum or average), signal power, or signal power spectrum slope. These primary signal features correlate with mass flow rate. Increases in signal power or amplitude in a bin over time indicate increases in volume of flow of particulates of the corresponding composition. If bins are not identically sized, sensor signals must be normalized according to bin size to reflect relative flow rates. Wider signal spread (i.e. flatter power spectrum slope) indicates a more sparsely populated bin, and thus a lower flow volume. Some embodiments of analysis module 32 analyze primary signal features to produce secondary signal features such as ratios of power or rates of change between bins. Secondary features are functions of primary features from multiple bins. Secondary features may, for instance, be second-order characteristics derived from primary features.

Some embodiments of signal analysis module 34 process time-domain sensor signals as well as frequency-domain sensor signals to extract features such as amplitude and peak number. In particular, time-domain sensor signals are used to recognize ingestion of individual discrete debris objects such as stones or detached bolts. Like frequency-domain signal features, time-domain signal features are broken down into a plurality of features which are forwarded to decision module 36.

Decision module 36 formulates the debris characterization from signal features extracted by signal analysis module 34. Amplitude, power, and power spectrum slope can all be used to estimate flow rate within each bin. In addition to providing a profile of mass flow rate as a function of composition, decision module 36 may also provide a quantitative confidence level indicating the statistical reliability of the debris characterization as a whole, or of each part of the debris characterization.

As previously discussed, some embodiments of debris monitoring system 10 include multiple debris sensors 22a and 22b. Signal analysis module 34 can separately extract features, including signal phase, from sensor signals of multiple sensors, just as described above with respect to a single sensor signal. Multiple sensors provide greater data volume, improving the resolution and confidence levels of the debris characterization. Additionally, some embodiments of signal analysis module 34 extract features reflecting relationships between multiple signals. Signal analysis module 34 may, for instance, determine particulate velocities by comparing time- or frequency-domain signals from debris sensors separated by a known distance. Particulate velocity generally diminishes with particulate size, and therefore provides a separate indication of particulate composition, which can be used by decision module 36 in addition to the feature characterization described above.

Debris monitoring system 10 produces more data at higher precision than purely time-domain based systems by analyzing both frequency- and time-domain signals. The addition of multiple debris sensors 22a and 22b further improves the quality and quantity of information produced by debris monitoring system 10.

Figure 2:
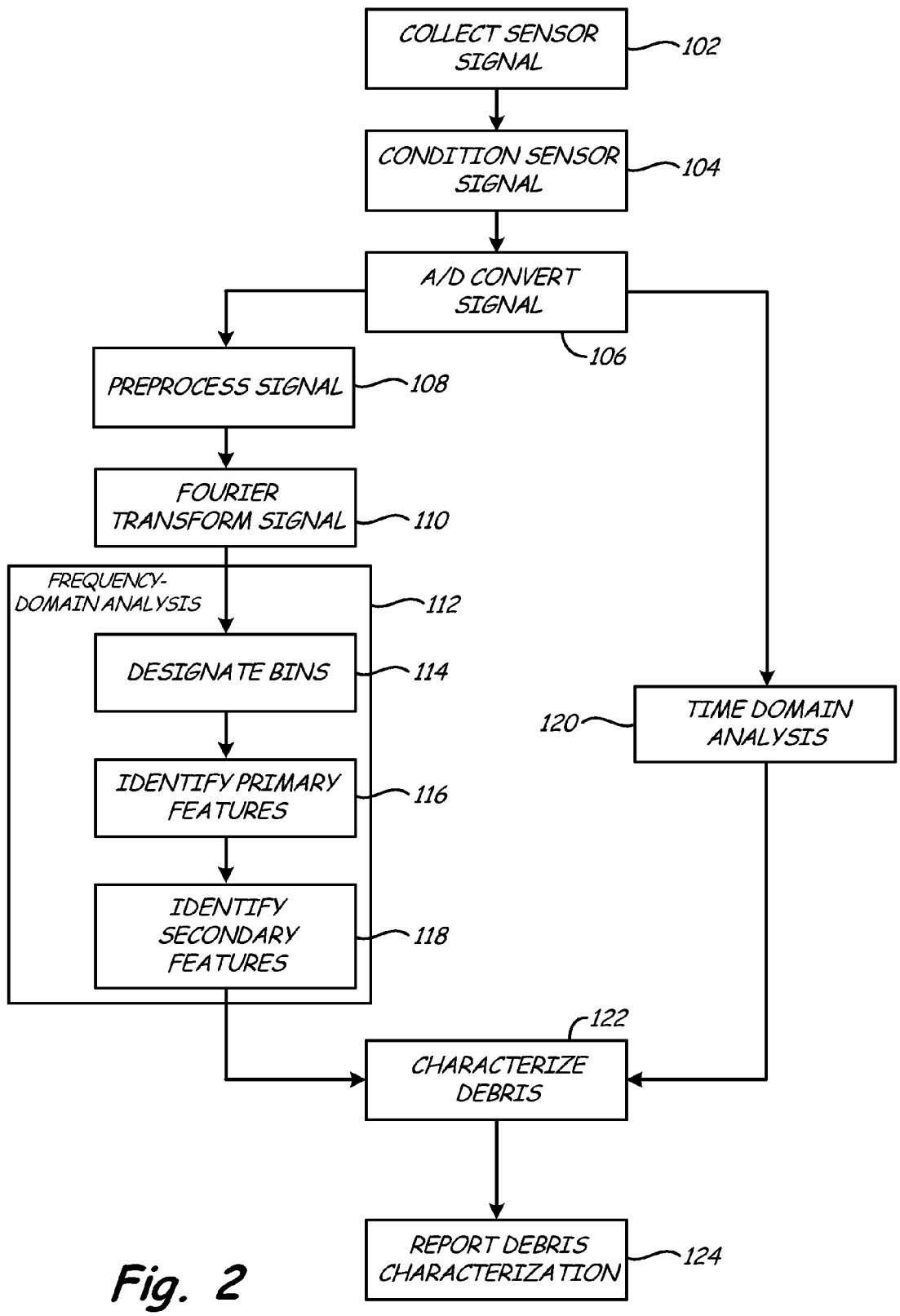
FIG. 2 is a flow chart depicting steps of a debris monitoring method performed by the debris monitoring system of FIG. 1.

FIG. 2 depicts steps of method 100 performed by debris monitoring system 10. First, debris sensors 22a and 22b continuously monitor debris passage to collect at least one sensor signal, as described above. (Step 102). Signal conditioner 24 and secondary signal conditioner 28 condition this sensor signal as described with respect to FIG. 1, filtering and amplifying it as needed. (Step 104). Analog/digital converter 30 translates the result into a digital signal. (Step 106). Signal preprocessor 32 applies additional filter functions dependent on the features to be extracted from the sensor signal by signal analysis module 34, as described above. (Steps 108).

In the depicted embodiment, time-domain and frequency-domain sensor signals are both analyzed by signal analysis module 34. Signal analysis module 34 Fourier transforms the digitized sensor signal (Step 110), and analyzes the resulting frequency-domain sensor signal to produce the debris characterization. (Step 112). As a first step of this analysis, the frequency-domain sensor signal is subdivided into a plurality of frequency range bins, which may be of fixed or variable width. (Step 114). Within each bin, signal analysis module 34 extracts a plurality of primary features, including signal amplitude, signal power, and signal power spectrum slope. (Step 116). Signal analysis module 34 next produces a series of secondary features, which reflect second-order properties derived from the primary features, such as energy ratios or rates or change. (Step 118). Secondary features may, for instance, include ratios of power or rates of change of primary features in different bins, or relationships between different primary features, such as amplitude and power.

In the depicted embodiment, signal analysis module 34 also analyzes time-domain sensor signals, as known in the prior art. (Step 120). To this end, signal analysis module 34 receives time domain-signals from signal preprocessor 32, and processes these signals to produces time-domain signal features such as the times and amplitudes of peaks corresponding to discrete debris ingestion events. Signal preprocessor 32 may filter signals for time-domain analysis, but the filter function applied for time-domain and frequency-domain preprocessing may differ. In some embodiments, signal analysis module 34 also determines debris velocities from either time- or frequency-domain signals.

Decision module 36 characterizes debris according to the primary and secondary features of the frequency-domain signal (Step 118), and reports a debris characterization which in some embodiments includes a quantitative confidence level. (Step 120). This debris characterization includes both times and average particulate flow profiles communicating mass flow rate as a function of particulate composition. The time resolution of the reported debris characterization can vary depending on the applications for which the debris characterization is to be used. At a minimum, the debris characterization includes an average profile of mass flow as a function of particulate composition, coupled with a timestamps reflecting the period covered by the characterization. For greater resolution, the debris characterization can include a plurality of such profiles over shorter time intervals. Each profile includes, at a minimum, a classification of flow rate for large and small particles. For greater precision, each profile may include a measured flow rate across a range of particle compositions categories. The debris characterization may also include timestamps and debris characterizations for discrete debris ingestion events determined using methods known in the art.

Figure 3:
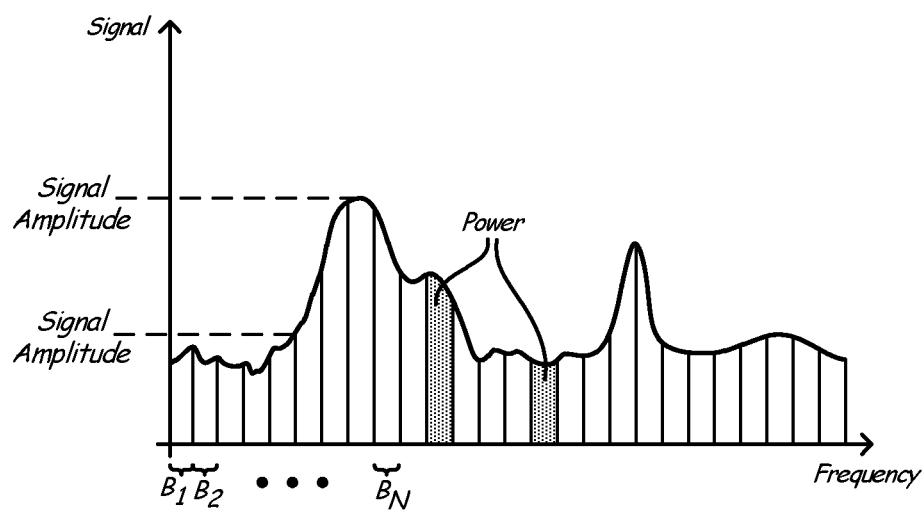
FIG. 3 is a graph of an example sensor signal as a function of frequency, indicating signal features monitored by the method of FIG. 2.

FIG. 3 is a graph of an example sensor frequency-domain sensor signal, and is not drawn to scale. FIG. 3 shows a plurality of bins $B_1$ through $B_N$ designated by signal analysis module 34. These bins are depicted as having regular widths covering a short frequency range, but may alternatively span irregular frequency ranges. Each bin corresponds to a range of particulate composition, such as range of particulate diameter or mass.

A variety of primary features may be assigned to each bin, such as signal amplitude or power, as shown. These features may comprise mean or median values within the bin, such as mean amplitude or median power spectrum slope. Each primary feature provides an indication of mass flow rate of particulates of a composition corresponding to the frequency range of the bin.

By analyzing debris sensor signals in the frequency domain, the present invention is able to characterize the composition of particulate debris. This characterization allows for more precise maintenance scheduling, reducing maintenance costs and improving aircraft safety. As noted above, prior art time-domain analysis may also be performed to recognize ingestion of individual discrete debris objects. By incorporating multiple debris sensors, the present invention is able to estimate particulate speed (and thereby size), and improve the precision and confidence level of debris characterizations.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A signal processing method for an inlet debris monitoring system, the method comprising:
retrieving time-domain signals from inlet debris sensors responsive to debris passing through an engine of an aircraft;
Fourier transforming the time-domain signals to produce a frequency domain sensor signal;
subdividing the frequency domain signal into bins corresponding to different particulate compositions; and
analyzing a feature of the frequency domain signal to determine particulate quantity and composition.

2. The method of claim 1, wherein the feature of the frequency domain signal comprises amplitude, power, or power spectrum rate of change.

3. The method of claim 1, wherein the analyzing is performed on the aircraft.

4. The method of claim 1, wherein the analyzing is performed at a location remote from the aircraft.

5. The method of claim 1, wherein the bins comprise frequency ranges of the frequency domain sensor signal.

6. The method of claim 5, wherein the frequency ranges are dynamically updated.

7. The method of claim 1, wherein the particulate composition determined comprises particulate size.

8. The method of claim 1, further comprising:
preprocessing either the time-domain signals or the frequency-domain sensor signal.

9. The method of claim 1, further comprising:
analyzing the time-domain signal to determine debris ingestion times and quantities.

10. A method for operating a debris monitoring system, the method comprising:
continuously sensing the passage of particulates through a gas turbine engine to produce a time-domain sensor signal;
Fourier transforming the time-domain sensor signal to produce a frequency domain sensor signal;
partitioning the frequency domain into frequency range bins corresponding to particulate composition categories;
identifying a plurality of primary features within each bin; and
determining the amount of particulate flow in each particulate composition category from the primary features identified within each corresponding bin.

11. The method of claim 10, further comprising:
identifying at least one secondary feature derived from the primary features across multiple bins; and evaluating the determination of particulate flow using the secondary feature.

12. The method of claim 10 further comprising:
identifying a plurality of time-domain features of the time-domain sensor signal; and
determining the time and extent of debris events using the time-domain features.

13. The method of claim 10, wherein the particulate composition categories reflect size of particulates.

14. The method of claim 10, wherein continuously sensing the passage of particulates comprises monitoring particulate passage through an inlet of the gas turbine engine.

15. The method of claim 10, wherein the plurality of primary features includes at least one of power, amplitude, phase, and power spectrum rate of change.

16. The method of claim 10, wherein the bins comprise frequency ranges of the frequency domain sensor signal.

17. An inlet debris monitoring system comprising:
an inlet debris sensor located at an inlet of a gas turbine engine to produce a sensor signal in response the passage of debris through the gas turbine engine;
a filter which removes noise and non-debris components from the sensor signal;
a signal analysis module which Fourier transforms the sensor signal, subdivides the sensor signal into bins, and identifies features of the sensor signal in each bin; and
a decision module which determines mass flow rate and particulate composition from the features in each bin.

18. The inlet debris monitoring system of claim 17, wherein the sensor is a electrostatic sensor which senses the passage of charged debris particles through a conductive ring.

19. The inlet debris monitoring system of claim 17, wherein the sensor is an analog sensor, and further comprising a signal conditioner and an analog-to-digital converter located between the sensor and the signal analysis module.

20. The inlet debris monitoring system of claim 17, further comprising at least one additional inlet debris sensor located at the inlet of the gas turbine engine to produce an additional sensor signal.

21. The inlet debris monitoring system of claim 20, wherein the signal analysis module separately identifies features of the sensor signal and the additional sensor signal, and wherein the decision module evaluates the features of both.

22. The inlet debris monitoring system of claim 20, wherein the signal analysis module identifies features derived from both the sensor signal and the additional sensor signal.

23. The inlet debris monitoring system of claim 22, wherein one of the features is a particulate speed determined from signal phase differences between the plurality of inlet debris signals.

* * * * *